US 8,974,424 B2
(12) United States Patent (10) Patent No.: US 8,974,424 B2
Soma et al. (45) Date of Patent: Mar. 10, 2015

(54) SYRINGE WITH PLUNGER LOCKING MECHANISM

(71) Applicant: Terumo Kabushiki Kaisha, Shibuya-ku (JP)

(72) Inventors: Katsuaki Soma, Fujinomiya (JP); Akihiro Takahashi, Ashigarakami-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/042,000

(22) Filed: Sep. 30, 2013

(65) Prior Publication Data

US 2014/0031763 A1 Jan. 30, 2014

Related U.S. Application Data

(63) Continuation of application No. PCT/JP2012/057238, filed on Mar. 21, 2012.

(30) Foreign Application Priority Data

Mar. 29, 2011 (JP) ................................. 2011-071922

(51) Int. Cl.
*A61M 5/315* (2006.01)
(52) U.S. Cl.
CPC ........... *A61M 5/31505* (2013.01); *A61M 5/315* (2013.01)
USPC .......................................... 604/220; 604/187
(58) Field of Classification Search
CPC .... A61M 5/3129; A61M 5/19; A61M 5/3158
USPC .......... 604/187, 191, 207–209, 214, 218, 220
See application file for complete search history.

(56) References Cited

U.S. PATENT DOCUMENTS

| 4,915,695 A | 4/1990 | Koobs |
| 5,009,645 A * | 4/1991 | Silver et al. ................... 604/207 |

(Continued)

FOREIGN PATENT DOCUMENTS

| JP | 101040 C2 | 6/1933 |
| JP | 60-138543 U | 9/1985 |

(Continued)

OTHER PUBLICATIONS

International Search Report (PCT/ISA/210) mailed on Jun. 26, 2012, by the Japanese Patent Office as the International Searching Authority for International Application No. PCT/JP2012/057238.

(Continued)

*Primary Examiner* — Theodore Stigell
*Assistant Examiner* — Amber Stiles
(74) *Attorney, Agent, or Firm* — Buchanan Ingersoll & Rooney PC

(57) ABSTRACT

The syringe includes first and second outer cylinders having a flowing port at a distal end through which liquid is flowable, and a plunger inserted from the proximal side of the outer cylinder. The syringe includes a tooth portion provided along the direction of movement of the plunger, and a hook configured to lock the tooth portion at a predetermined locking position and prevent the movement of the plunger in the direction toward the proximal end. The hook retracts from the locking position in association with the unlocking operation and restores automatically to the locking position after the unlocking operation.

12 Claims, 8 Drawing Sheets

(56) References Cited

U.S. PATENT DOCUMENTS

| | | | |
|---|---|---|---|
| 5,246,011 A * | 9/1993 | Caillouette | 600/566 |
| 5,380,295 A | 1/1995 | Vacca | |
| 5,385,558 A * | 1/1995 | Cottone et al. | 604/208 |
| 2003/0120217 A1 | 6/2003 | Abergel | |
| 2004/0122361 A1 | 6/2004 | Hart et al. | |
| 2008/0275403 A1 * | 11/2008 | Maaskamp et al. | 604/191 |
| 2013/0023885 A1 * | 1/2013 | Madden et al. | 606/93 |

FOREIGN PATENT DOCUMENTS

| | | |
|---|---|---|
| JP | 61-30698 U | 2/1986 |
| JP | 8-504352 A | 5/1996 |

OTHER PUBLICATIONS

European Search Report mailed on Sep. 25, 2014, by the European Patent Office in corresponding European Patent Application No. 12765675.9 (5 pages).

\* cited by examiner

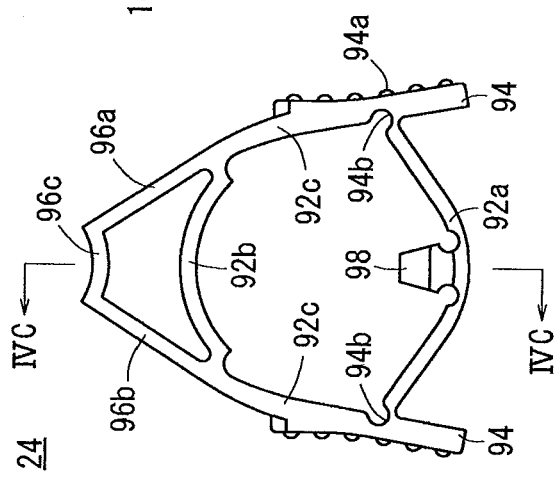
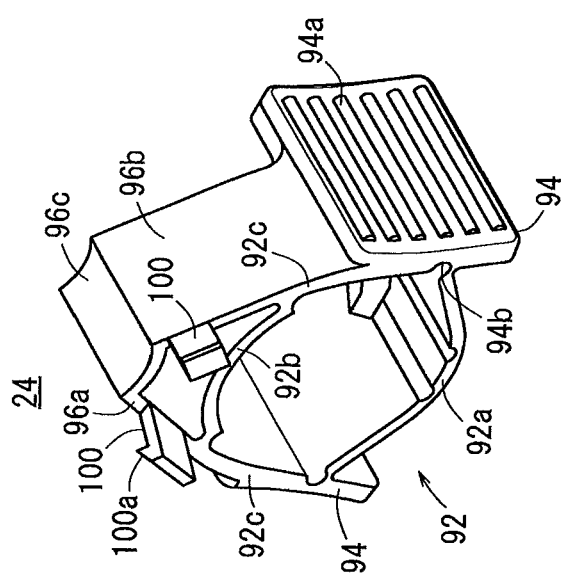

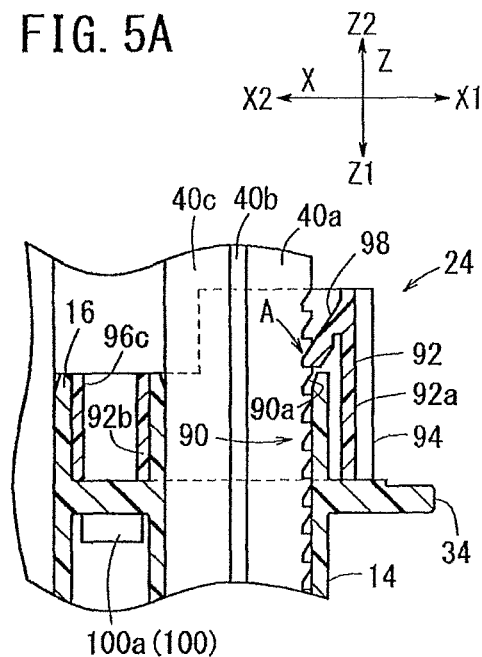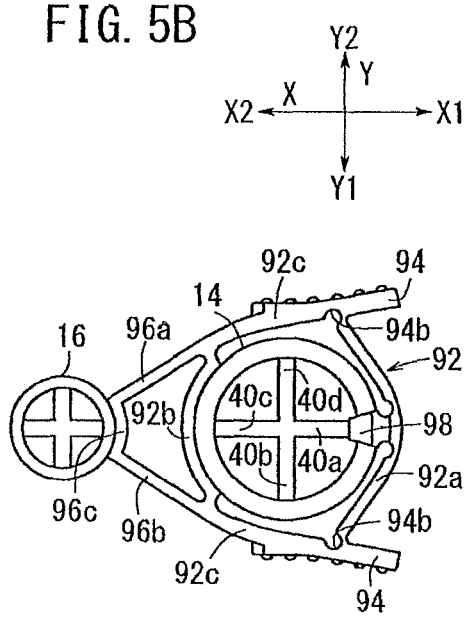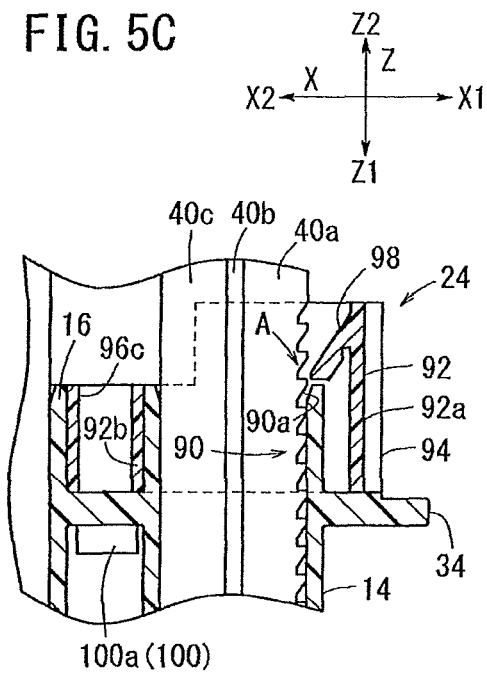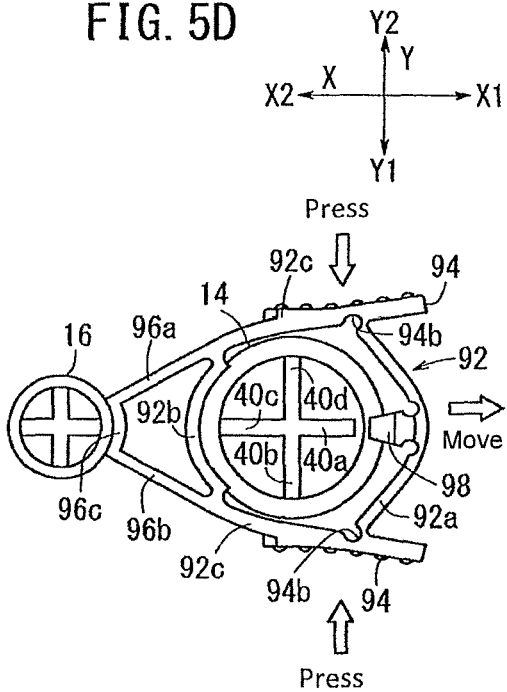

SYRINGE WITH PLUNGER LOCKING MECHANISM

CROSS REFERENCES TO RELATED APPLICATIONS

This application is a continuation of International Application No. PCT/JP2012/057238 filed on Mar. 21, 2012, and claims priority to Japanese Application No. 2011-071922 filed on Mar. 29, 2011, the entire content of both of which is incorporated herein by reference.

TECHNICAL FIELD

The present invention generally relates to a syringe configured to discharge liquid filled in an outer cylinder by the movement of a plunger.

BACKGROUND DISCUSSION

In medical facilities or the like, for example, when administering medicinal solution such as an adhesion prevention agent or a body tissue adhesive agent to an affected area, the medicinal solution is discharged by using a syringe. In this case, the medicinal solution diluted or dissolved with liquid is sucked into and fills the outer cylinder of the syringe by moving the plunger in the direction toward a proximal end of the outer cylinder, and the medicinal solution is discharged from a flowing port provided at a distal end of the outer cylinder by moving the plunger in the direction toward the distal end of the outer cylinder.

In the syringe configured in this manner, a configuration is required so that the plunger cannot be pulled out from the outer cylinder (cannot be moved in the direction toward the proximal end) in a state in which the outer cylinder is filled with the medicinal solution (liquid). If the plunger is pulled out, there is a probability that non-filled substance (for example, air, gas, and the like) of an external environment enters the interior of the outer cylinder and causes contamination or deterioration of the filled liquid. In addition, if the plunger comes apart from the outer cylinder by being pulled out, the filled liquid may inconveniently spill out.

Japanese Application Publication No. 8-504352 discloses a structure to prevent the movement of the plunger in the direction toward the proximal end that includes a tooth portion (ratchet gear) on a side surface of the plunger and a movement stop device configured to engage the tooth portion. Accordingly, the movement stop device locks the tooth portion and hence the movement of the plunger inserted into the outer cylinder in the direction toward the proximal end is prevented.

However, from the syringe disclosed in JP-T-8-504352, a method of movement of the plunger when filling the outer cylinder with liquid cannot be estimated. In other words, since the tooth portion is locked to the movement stop device in the configuration of the syringe disclosed in JP-T-8-504352, the movement of the plunger in the direction toward the proximal end which is performed when filling the syringe with the liquid cannot be performed easily.

SUMMARY

According to one aspect, a syringe includes: an outer cylinder having a flowing port at a distal end of the outer cylinder through which liquid flows, a plunger insertable into the outer cylinder from a proximal end of the outer cylinder to push out the liquid in the interior of the outer cylinder through the flowing port by movement of the plunger in a movement direction toward the distal end of the outer cylinder; a tooth portion provided on the plunger and arranged along the movement direction of the plunger; and a locking portion configured to lock the tooth portion at a locking position to prevent the plunger from moving in a proximal direction away from the distal end of the outer cylinder. The locking portion is retracted from the locking position in response to an unlocking operation, and is automatically restored to the locking position after the unlocking operation.

The syringe is able to reliably prevent movement of the plunger in the direction toward a proximal end in a state in which the outer cylinder is filled with liquid, and perform filling of the outer cylinder with the liquid while allowing the movement of the plunger in the direction toward the proximal end by a rather simple operation, thereby improving an operation efficiency at the time of handling significantly.

The locking portion configured to lock the tooth portion is retracted from the locking position in association with the unlocking operation, and hence the movement of the plunger in the direction toward the proximal end is allowed, and the outer cylinder may be filled rather easily with the liquid. Also, the locking portion is capable of locking the tooth portion relatively easily without performing an additional operation by restoring automatically to the locking position after the unlocking operation. Accordingly, the movement of the plunger in the direction toward the proximal end in a state in which the liquid is filled is reliably prevented, and the non-filled substance is prevented from entering the outer cylinder. Therefore, the working efficiency when treating the syringe is significantly improved.

The locking portion can include a hook molded integrally with a flexible stopper member, and the stopper member arranges the hook at the locking position by being mounted on the outer cylinder.

The stopper member formed with the hook in this manner is mounted on the outer cylinder, so that the hook can be arranged rather easily at the locking position, whereby the movement of the plunger in the direction toward the proximal end is prevented by the hook. In addition, by molding the stopper member as a separate member so as to be demountably mountable, the stopper member can be removed fairly easily in a circumstance in which the stopper member is not required and, in addition, the shape of the outer cylinder of the related art is not significantly changed at the time of molding, so that the manufacturing cost can be reduced.

The stopper member can also include: a mounting portion configured to surround an outer peripheral surface of the outer cylinder, and a set of operating sections extending so as to be apart radially outward from an outer peripheral surface of the mounting portion, wherein the hook is formed on an inner peripheral surface of the mounting portion, moves radially outward under a pinching action of the set of the operating sections at the time of unlocking operation and retracts from the locking position is also applicable.

In this manner, with the configuration in which the hook moves radially outward under the pinching operation of a set of the operating sections and is retracted from the locking position, the hook can be retracted from the locking position only by pinching the operating sections of the stopper member at the time of unlocking operation, and hence the movement of the plunger in the direction toward the proximal end is rather easily allowed.

In addition, the mounting portion is preferably provided with a supporting portion configured to suppress radially outward movement at a position on a side opposite to the position where the hook is formed.

By suppressing the movement of the position of the mounting portion on a side opposite to the position on the mounting portion where the hook is formed by the supporting portion, when the set of operating sections are pinched, the portion on the opposite side is supported (the movement is suppressed). Therefore, the pinching force is desirably transmitted to the mounting portion on the side where the hook is formed, so that the hook can be reliably retracted from the locking position.

The syringe can be configured to include a plurality of outer cylinders arranged side by side so that the directions of the axes of the outer cylinders extend parallel to each other, and the supporting portion includes an abutting portion extending toward the outer cylinder different from the outer cylinder on which the stopper member is mounted and coming into abutment with the different cylinder.

The movement of the position on the side opposite to the position where the hook is formed can be suppressed easily by the abutment of the abutting portion against the separate outer cylinder. Also, the movement of the stopper member in the direction of rotation can be prevented by the abutment and the engagement of the abutting portion with the separate outer cylinder, and the hook can be arranged reliably at the locking position.

The outer cylinder includes a flange extending radially outward and formed on the side of the proximal end of the outer cylinder, and the flange is provided with a hole portion at a predetermined position, while the supporting portion includes a projecting portion inserted into the hole portion.

Inserting the projecting portion into the hole portion of the flange allows the portion on the side opposite to the position where the hook is formed to be fixed further reliably, so that the movement of the position on the opposite side can be suppressed.

The locking portion can include a hook molded integrally with the stopper member, with the stopper member including a mounting portion formed with the hook on an inner peripheral surface of the mounting portion and being slidable in the direction orthogonal to the outer cylinder, and a resilient member configured to urge the mounting portion in the predetermined direction, wherein the mounting portion retracts the hook from the locking position by sliding movement in the direction opposite to the predetermined direction and restores the hook to the locking position by the resilient member after the retraction.

In this manner, with the provision of the resilient member configured to urge the mounting portion, the mounting portion is slid in the direction opposite to the urging direction of the resilient member, and the mounting portion is slid by being urged by the resilient member, whereby the hook can be automatically restored to the locking position. Accordingly, prevention of the movement of the plunger and allowing of the movement in the direction toward the proximal end can be switched rather easily.

According to another aspect, a syringe comprises: an outer cylinder possessing a distal end and a flowing port at the distal end of the outer cylinder through which liquid flows, with the outer cylinder possessing an open proximal end and an inner surface surrounding an interior of the outer cylinder, the interior of the outer cylinder communicating with the flowing port, and the outer cylinder possessing an outer surface; a gasket positioned in the interior of the outer cylinder in liquid-tight contact with the inner surface of the outer cylinder and movable in a distal direction along the interior of the outer cylinder to discharge the liquid, which was previously introduced into the interior of the outer cylinder, through the flowing port; a rod connected to the gasket so that the rod and the gasket move together as a unit, with the rod extending through the open proximal end of the outer cylinder, and with the rod including a plurality of teeth arranged in spaced apart relation along the rod; and a mounting portion surrounding a proximal end portion of the outer cylinder and possessing an inner surface facing the outer surface of the outer cylinder. A hook is fixed to the mounting portion and extends inwardly, with the hook engaging one of the teeth on the rod in a locking position of the hook to prevent the rod from moving in the proximal direction relative to the outer cylinder. An operating portion is fixed to the mounting portion and is operable by a user pressing the operating portion to move the hook from the locking position in which the hook engages one of the teeth to an unlocking position in which the hook is moved out of engagement with the teeth to permit the rod to move in the proximal direction, the hook automatically returning to the locking position when the operating portion is no longer pressed by the user.

BRIEF DESCRIPTION OF DRAWINGS

FIG. 4A is a perspective view of a stopper member in FIG. 1, FIG. 4B is a front view of a stopper member in FIG. 1, and FIG. 4C is a cross-sectional view taken along the section line IVC-IVC in FIG. 4B.

FIG. 5A is a partially enlarged cross-sectional view illustrating the stopper member in FIG. 1 and a peripheral portion thereof in an enlarged scale, FIG. 5B is a cross-sectional front view corresponding to FIG. 5A, FIG. 5C is a partially enlarged cross-sectional view illustrating a state in which a hook of the stopper member in FIG. 1 moves apart in an enlarged scale, and FIG. 5D is a cross-sectional front view corresponding to FIG. 5C.

DETAILED DESCRIPTION

Figure 1:
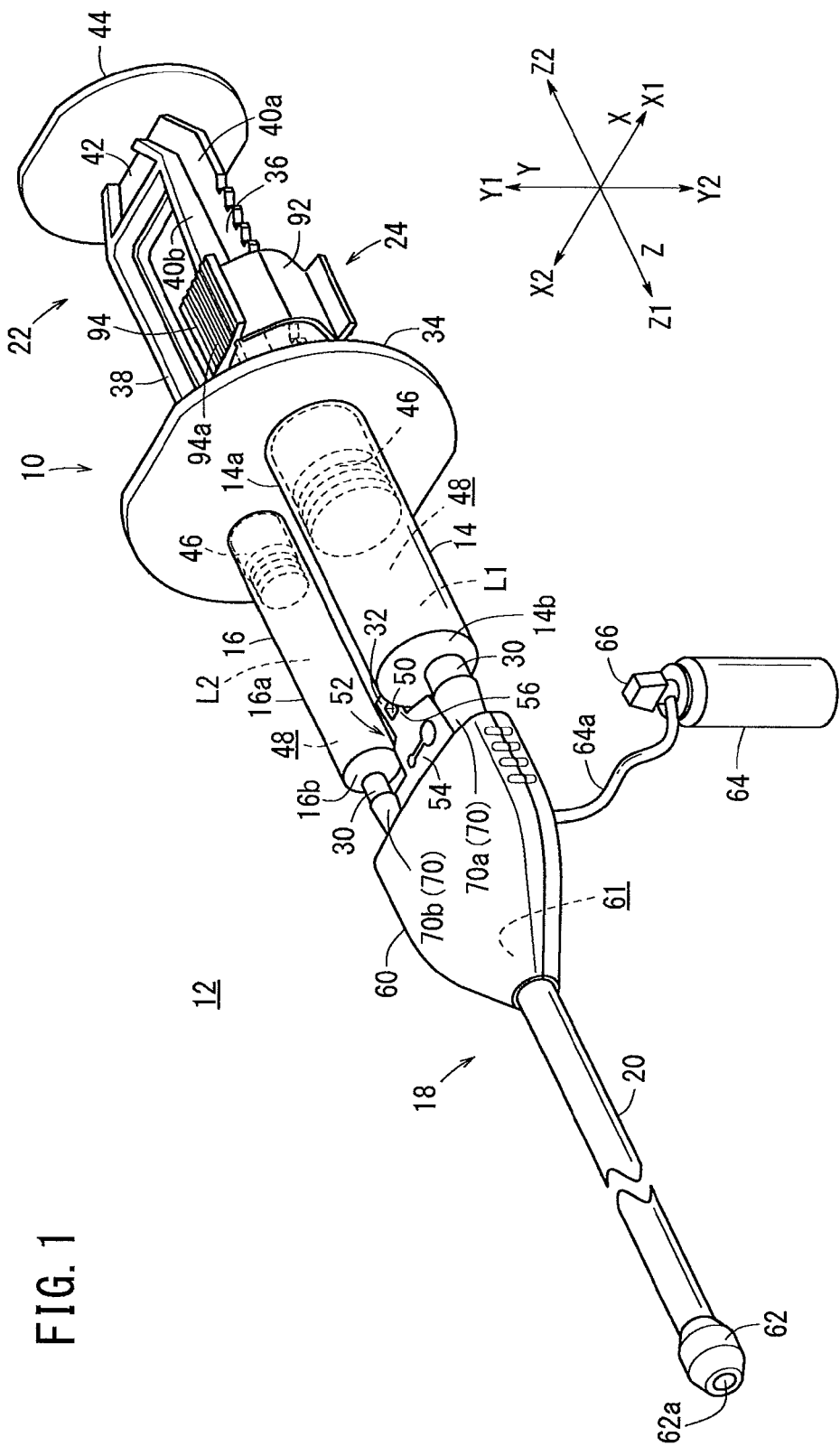
FIG. 1 is a schematic perspective view of the overall configuration of an application instrument having a syringe according to a first embodiment.

Referring now to the accompanying drawings, a syringe according to one embodiment disclosed by way of example will be described in detail. FIG. 1 illustrates the syringe 10. In the following explanation, the syringe is described by way of example as a part of an application instrument 12. However, the syringe is not limited to this use, and it may be applied to a generally known injection or the like as a matter of course.

The application instrument 12 according to the first embodiment is a spray-type device provided with the syringe 10. The application instrument 12 includes a first outer cylinder 14 and a second outer cylinder 16 arranged side by side and integrally coupled, and a nozzle 18 configured to cause the syringe 10 to discharge liquid filled in the syringe 10 to an object to which the liquid is to be applied by a connection between respective distal ends of the first and second outer cylinders 14, 16. The application instrument 12 is a medical instrument configured to be used by inserting a thin and elongated nozzle body 20 extending in the direction toward a distal end of the nozzle 18, mixing two types of liquid supplied from the syringe 10 and having different liquid compositions, and simultaneously applying a medicinal solution as the mixture to an internal organ or an abdominal wall or the like in a case of a laparoscopic surgery, for example.

In the following description, the width direction of FIG. 1 is referred to as the X-direction, the height direction is referred to as the Y-direction, and the direction of extension of the outer cylinder is referred to as the Z-direction (axial direction). Also, The front (discharging direction) of the outer cylinder is referred to as Z1-direction or a distal end, and the back of the outer cylinder is referred to as Z2 direction or a proximal end (rear end). In addition, the rightward direction when viewing the application instrument 12 from the distal end side is referred to as the X1 direction, the leftward direction is referred to as of the outer cylinder X2 direction, the upward direction is referred to as of the outer cylinder Y1 direction, and the downward direction is referred to as of the outer cylinder Y2 direction. For reference, these directions are simply for the sake of convenience for explanation and, the application instrument 12 can be used in a given direction (for example, upside down) as a matter of course.

As illustrated in FIG. 1, the syringe 10 includes the first outer cylinder 14 and the second outer cylinder 16 which contain or are to be respectively filled with two types of liquids to be mixed at the nozzle 18 and discharged from the nozzle, a bifurcated plunger 22 positioned in the first and second outer cylinders 14, 16 from proximal ends of the first and second outer cylinders 14, 16, and a stopper member 24 mounted on the first outer cylinder 14. For reference, in the case of this embodiment, the first outer cylinder 14 and the second outer cylinder 16 have substantially the same configuration except for differences in the outer diameter and the internal capacity. Therefore, in the following description, the first outer cylinder 14 will be described as a representative of the two outer cylinders, and such description also applies to the second outer cylinder 16. The first outer cylinder 14 and the second outer cylinder 16 may have the same diameter.

Figure 2:
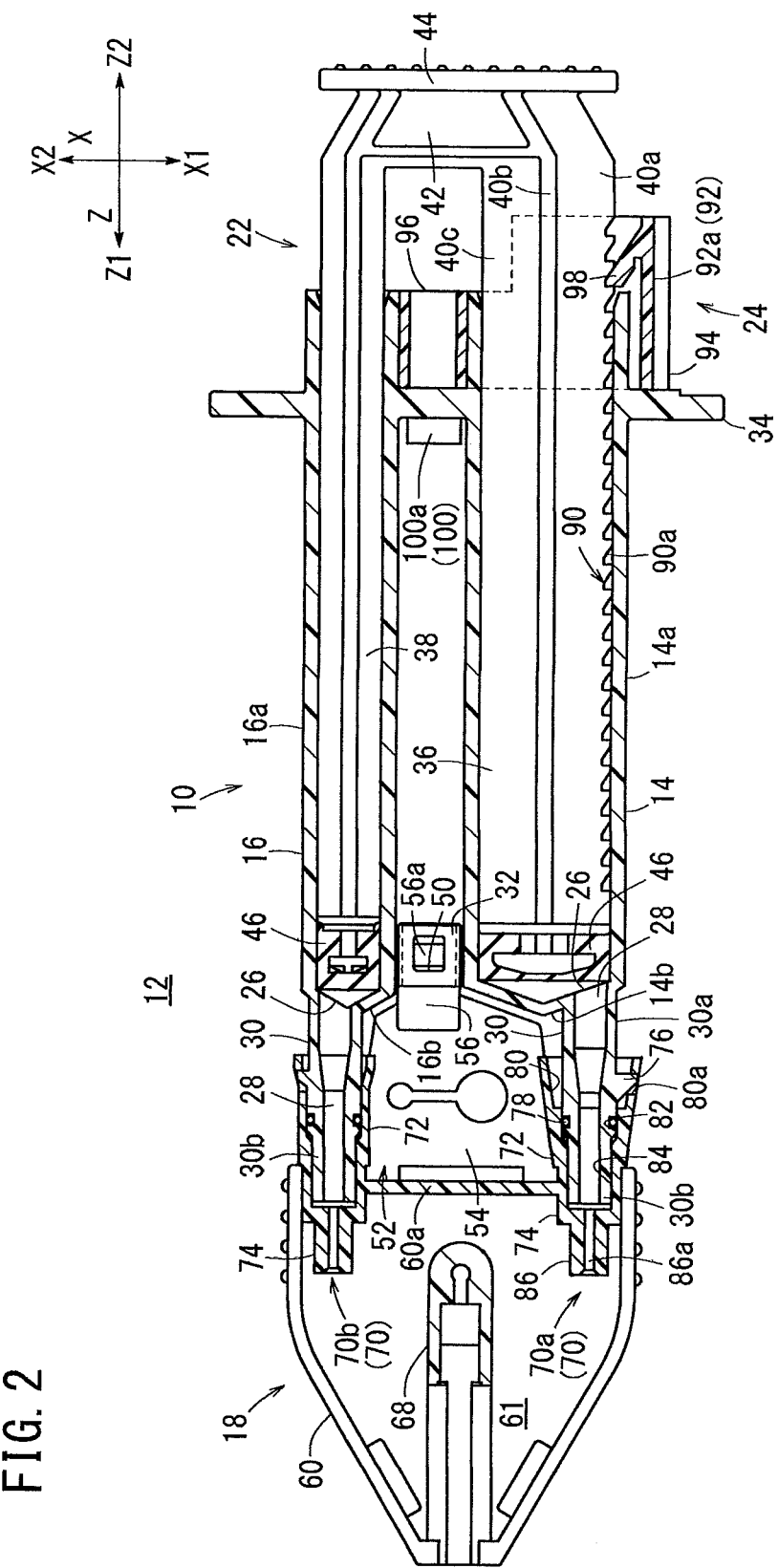
FIG. 2 is a partially cross-sectional plan view illustrating an application instrument 12 in FIG. 1.

As illustrated in FIG. 1 and FIG. 2, the first outer cylinder 14 is formed so that the cylindrical portion 14a extends in the Z direction, and a distal end portion 14b continuing to the cylindrical portion 14a possesses a bottomed cylindrical shape decreasing in outer diameter in a tapering manner. The distal end portion 14b includes a flowing port (port) 26 at a predetermined position (on the side of the X1 direction) and, in addition, is provided with a projecting portion 30 having a flowing channel (channel) 28 communicating with the flowing port 26 so as to project in the Z1 direction. The cylindrical portion 14a is formed integrally with a flat plate shaped coupling portion 32 extending from the outer peripheral surface in the X2 direction at a portion near the distal end of the cylindrical portion, and the coupling portion 32 couples the first and second outer cylinders 14, 16 to each other.

In addition, the outer peripheral surface of the first outer cylinder 14 on the proximal end is integrally formed with a thin-plate oval-shaped flange 34 extending in the radially outward direction, so that an operator can hook his index finger or middle finger or the like on the flange 34 when operating the plunger 22. The flange 34 also extends toward the second outer cylinder 16 and is integrated also with the outer peripheral surface of the second outer cylinder 16. In other words, the syringe 10 is configured to support the parallel relationship between the first outer cylinder 14 and the second outer cylinder 16 by the coupling portion 32 and the flange 34.

The material constituting the first and second outer cylinders 14, 16 is not specifically limited and examples of materials include resins such as polyvinyl chloride, polyethylene, polypropylene, cyclic polyolefin, polystyrene, poly-(4-methyl penten-1), polycarbonate, acrylic resin, acrylonitrile-butadiene-styrene copolymer, polyester such as polyethylene terephthalate and polyethylene naphthalate, butadiene-styrene copolymer, polyamide (for example, nylon 6, nylon 6.6, nylon 6.10, and nylon 12) may be used. Alternatively, when considering the easiness of molding, low vapor permeability, and the like, polypropylene, cyclic polyolefin, polyester, and the like are preferable. In order to secure the visibility of the interiors, the first and second outer cylinders 14, 16 are preferably transparent or translucent.

The plunger 22 of the syringe 10 includes a first rod 36 inserted into the first outer cylinder 14 from a proximal opening portion of the first outer cylinder 14 and a second rod 38 inserted into the second outer cylinder 16 from a proximal opening portion of the second outer cylinder 16. The first and second rods 36 and 38 each have four flat plate portions 40a to 40d extending outwardly from a center axis to form a cross-shape with the center axis of the rod in front cross-sectional view such as seen in FIG. 5B. The respective flat plate portions 40a to 40d extend in the axial direction to possess a predetermined length in the axial direction (Z-direction).

The distal ends of the first and second rods 36 and 38 are integrally coupled or connected by a bridge 42, and the first and second rods 36 and 38 with the bridge 42 together form a substantially U-shape as a whole. In other words, the forward and rearward movement of the plunger 22 is integrally performed by the common operating portion (operating disk) 44 provided on the bridge 42. Although the material of the plunger 22 may be the same as that of the first and second outer cylinders 14, 16, a non-transparent material is preferable in order to improve the visibility in the transparent outer cylinder.

Also, a gasket 46 formed of a resilient material is mounted at a distal end of each of the first and second rods 36, 38. The gaskets 46 are configured to be slidable in a liquid-tight manner in tight contact with the inner peripheral surface of the respective first and second outer cylinders 14, 16. In other words, the gasket 46 moves integrally with the forward and rearward movement of the plunger 22, and changes the capacity of the filling chamber 48 (see FIG. 1) defined by the distal end surface of the gasket 46, the inner peripheral surface of the cylindrical portion 14a, and the distal end portion 14b. The syringe 10 is capable of sucking in (drawing in) liquid to fill the filling chambers 48 with liquid in association with the movement of the plunger 22 in the direction toward the proximal end (pulling operation), and pushing out the liquid in the filling chambers 48 from the flowing port 26 in association with the movement (pushing operation) of the plunger 22 in the distal direction.

The material of the gasket 46 is not specifically limited. Examples of materials which may be used include resilient material such as, for example, various types of rubbers such as natural rubber, butyl rubber, isoprene rubber, butadiene rubber, styrene-butadiene rubber, silicone rubber, polyurethane-based, polyester-based, polyamide-based, olefin-based and styrene-based various thermoplastic elastomers, and a mixtures thereof.

The second outer cylinder 16 has substantially the same configuration as the first outer cylinder 14 described above, and includes the cylindrical portion 16a, the distal end portion 16b, and the projecting portion 30, and the second rod 38 is positioned in the second outer cylinder by being inserted from the proximal opening portion of the second outer cylinder. As described above, the second outer cylinder 16 is also integrated with or connected to the flange 34 commonly with the first outer cylinder 14.

The first and second outer cylinders 14, 16 are coupled by the coupling portion 32 at the outer peripheral surfaces near the distal ends of the cylindrical portions 14a, 16a. The coupling portion 32 is provided with a locking hole 50 which constitutes an engaging mechanism for locking and unlocking the first and second outer cylinders 14, 16 when mounting and dismounting the nozzle 18 with respect to the syringe 10. The engaging mechanism includes the locking hole 50 and an engagement extending portion 52 provided on the nozzle 18 side.

The engagement extending portion 52 includes a proximal end extending strip 54 extending from the proximal end of the nozzle 18 in the proximal direction toward the proximal end of the outer cylinder (Z2 direction) and an engaging strip 56 projecting further in the proximal direction toward the proximal end from the proximal end extending strip 54. The engaging strip 56 is formed, at a predetermined position of the engaging strip 56, with a projection 56a configured to engage the locking hole 50, and in the mounting state between the syringe 10 and the nozzle 18, the projection 56a is caught by the locking hole 50. Accordingly, the mounting state between the syringe 10 and the nozzle 18 may be maintained. Also, the engagement extending portion 52 is formed of a material having flexibility (for example, a synthetic resin), and is capable of resiliently maintaining the locking condition between the projection 56a and the locking hole 50.

In the syringe 10, the first outer cylinder 14 contains the first liquid L1 and the second outer cylinder 16 contains the second liquid L2. The liquids L1, L2 may be selected as needed according to the application, the object of usage or the like of the application instrument 12 and, for example, when used for administering the body tissue adhesive agent, one of the first liquid L1 and the second liquid L2 may be liquid (solution or the like) containing thrombin and the other one may be liquid (solution or the like) containing fibrinogen. Also, when the application instrument 12 is used for administering the adhesion preventing agent for example, one of the first liquid L1 and the second liquid L2 may be liquid (solution or the like) containing NHS dextrin modified by Succinimidyl group and the other one may be liquid (solution or the like) containing sodium carbonate and sodium hydrogen carbonate.

When the first liquid L1 and the second liquid L2 in this combination is transformed, that is, turned into a gel (solidified) when mixed. By turning into a gel, for example, when the mixed medicinal solution (mixed substance, mixed liquid) may be retained reliably on the body tissue (intended portion) where it is applied, so that the function as the body tissue adhesive agent or the adhesion prevention agent is reliably achieved. As a matter of course, the type and combination of the first and second liquids L1, L2 are not limited to those described above by way of example.

The nozzle 18 includes the elongated nozzle body 20, a nozzle supporting portion 60 supporting the proximal portion of the nozzle body 20, and a nozzle head 62 provided at a distal end of the nozzle body 20 as illustrated in FIG. 1. The nozzle body 20 includes a nozzle flow channel in which the first liquid L1 supplied from the first outer cylinder 14, the second liquid L2 supplied from the second outer cylinder 16, and sterile gas supplied from a tank 64 (hereinafter, referred to simply as "gas") are mixed and integrally flow together.

The tank 64 illustrated as an example of the configuration of the gas supply source is filled with high-pressure (compressed) gas in the interior of the tank 64, and is capable of supplying (feeding) gas to the application instrument 12 (nozzle 18). Air (for example, oxygen or carbon dioxide) may be used as the gas. The tank 64 is provided with a valve (cock) 66 configured to be openable and closable to control the gas between supply and supply stop with respect to the application instrument 12. When using the application instrument 12, the valve 66 is brought into an opened state.

The nozzle head 62 has an outer shape, columnar-shaped in this illustrated embodiment disclosed by way of example, and includes a projection port 62a at a distal end portion of the nozzle head 62. The nozzle flow channel communicates with the projection port 62a. The projection port 62a functions as an opening portion for discharging a mixture of the first liquid L1, the second liquid L2 and the gas mixed in the nozzle flow channel.

The nozzle supporting portion 60 is a box-shaped member (housing member) including a metallic material or a resin material, for example, is formed into a substantially triangular shape tapered in plan view, and includes a circular opening which allows insertion of the nozzle body 20 at a distal end of the nozzle supporting portion 60. The nozzle supporting portion 60 is provided with an internal space 61 which is configured to store certain amounts of the first and second liquids L1, L2 in the box-shaped housing. The internal space 61 is provided with a gas port 68 to which a tube 64a extending from the tank 64 is inserted and connected at a center portion of the lower surface side of the internal space 61. Also, the lateral direction of the proximal end side of the nozzle supporting portion 60 is provided with a pair of mount holders 70 (a first mounting holder 70a and a second mounting holder 70b) in which the projecting portions 30 of the syringe 10 are inserted.

As illustrated in FIG. 2, the first mounting holder 70a in which the projecting portion 30 of the first outer cylinder 14 is inserted or positioned includes an outer mounting portion 72 projecting rearward (in the Z2 direction) from the proximal end wall portion 60a of the nozzle supporting portion 60 with at least its inner diameter increasing (both the inner and the outer diameters are increasing in the illustrated embodiment), and an inner mounting portion 74 continuing to the proximal end wall portion 60a of the nozzle supporting portion 60 in the interior of the nozzle supporting portion 60. Since the second mounting holder 70b in which the projecting portion 30 of the second outer cylinder 16 is inserted or positioned also has the substantially same configuration and function as the first mounting holder 70a, the description of the first mounting holder 70a applies equally to the second mounting holder 70b and so the description will not be repeated.

Here, the projecting portion 30 of the first outer cylinder 14 includes a first extending portion 30a extending from the proximal end side continuing to the cylindrical portion 14a in the direction toward the distal end and a second extending portion 30b continuing to the first extending portion 30a and extending in the direction toward the distal end with at least its outer diameter reduced (both the inner and outer diameters are reduced in the illustrated embodiment) in comparison with the first extending portion 30a. The side surface of the first extending portion 30a in the X1 direction is formed with a projecting portion 76 projecting outward. The projecting portion 76 is formed with a groove portion on the distal end side and an O-ring 78 is fitted into the groove portion.

The outer mounting portion 72 of the first mounting holder 70a includes a depression or hole 80 opening toward the proximal end, a first fitting hole 82 reduced in inner diameter in the radially inward direction with respect to the bottom surface of the depression 80, and a second fitting hole 84 reduced in inner diameter further from the first fitting hole 82 corresponding to the outer shape formed into a tapered shape. The depression 80 is formed into a tapered shape reduced in inner diameter from the opening at the proximal end toward the distal end, and the depression 80 is formed with a hooking hole 80a on the side surface in the X1 direction. In the state of mounting of the syringe 10 and the nozzle 18, the projecting portion 76 is caught by the hooking hole 80a, whereby the projecting portion 30 is prevented from coming apart from the first mounting holder 70a.

Also, the first fitting hole 82 is formed so as to substantially match the first extending portion 30a in terms of the inner diameter. In the state in which the syringe 10 and the nozzle 18 are mounted, the distal end of the first extending portion 30a fits into (is located in) the first fitting hole 82 and, in this state, the O-ring 78 comes into tight contact with the first fitting hole 82. Accordingly, the distal end side of the projecting portion 30 is hermetically closed by the O-ring 78.

Furthermore, the second fitting hole 84 is formed so as to substantially match the position of the second extending portion 30b in terms of the inner diameter. In the state in which the syringe 10 and the nozzle 18 are mounted, the second extending portion 30b is configured to fit into (is located in) the second fitting hole 84.

The inner mounting portion 74 of the first mounting holder 70a shares or includes the second fitting hole 84 in the proximal end side. An inner projecting portion 86 provided with a guiding flow channel 86a opening so as to face the flowing channel 28 of the projecting portion 30 and communicating to the internal space 61 of the nozzle supporting portion 60 is formed at a distal end of the second fitting hole 84. In other words, the flowing channel 28 of the projecting portion 30 communicates with the guiding flow channel 86a by mounting the syringe 10 and the nozzle 18, and when discharging the first liquid L1 in the first outer cylinder 14, the first liquid L1 flows into the internal space 61 of the nozzle supporting portion 60 via the flowing channel 28 and the guiding flow channel 86a.

When the projecting portion 30 of the first outer cylinder 14 is inserted into the first mounting holder 70a, the second extending portion 30b enters the second fitting hole 84 of the inner mounting portion 74. At this time, increase in diameter of the second fitting hole 84 of the inner mounting portion 74 is prevented due to the existence of the proximal end wall portion 60a in the side surface direction (X direction). Therefore, the second extending portion 30b is reliably fitted and held.

Also, when the projecting portion 30 of the first outer cylinder 14 is inserted into the first mounting holder 70a, the distal end side of the first extending portion 30a and the first fitting hole 82 fit together. In addition, the projecting portion 76 is inserted into the hooking hole 80a of the depression 80 and hence is caught by the hooking hole 80a. Also, in this state, coupling between the syringe 10 and the nozzle 18 is reliably achieved by the projection 56a locked in the locking hole 50 formed on the coupling portion 32 of the syringe 10.

Set forth next is a description of the stopper member 24 mounted to the application instrument 12 (the syringe 10), and a tooth portion 90 engaging the stopper member 24 (hereinafter, the stopper member 24 and the tooth portion 90 are collectively referred to also as a movement preventing mechanism).

The tooth portion 90 is formed on the flat plate portion 40a extending in the X1 direction of the first rod 36. Specifically, the tooth portion 90 is formed on a side edge portion in the X1 direction of the flat plate portion 40a as a saw-toothed rack (rack) including a plurality of teeth 90a arranged continuously one after another. In this case, the teeth 90a are configured so that the distal side or front end of the tooth is inclined and the proximal side or rear end side is orthogonal to the axis of the rod. Here, the intervals of the plurality of teeth 90a (the spacing between axially adjacent teeth) may be formed so as to be proportional to a predetermined capacity unit of the filling chambers 48 of the first liquid L1 (the distal end surface of the gasket 46, the inner peripheral surface of the cylindrical portion 14a, and a chamber formed by the distal end portion 14b). For example, when the filling chambers 48 has a capacity of 100 ml, if the plurality of teeth 90a are formed at intervals so as to change the capacity in increments or decrements of 5 ml, the first liquid L1 can be pushed out at a unit of 5 ml when pushing the plunger 22, so that a desired amount of liquid can be discharged.

Figure 3:
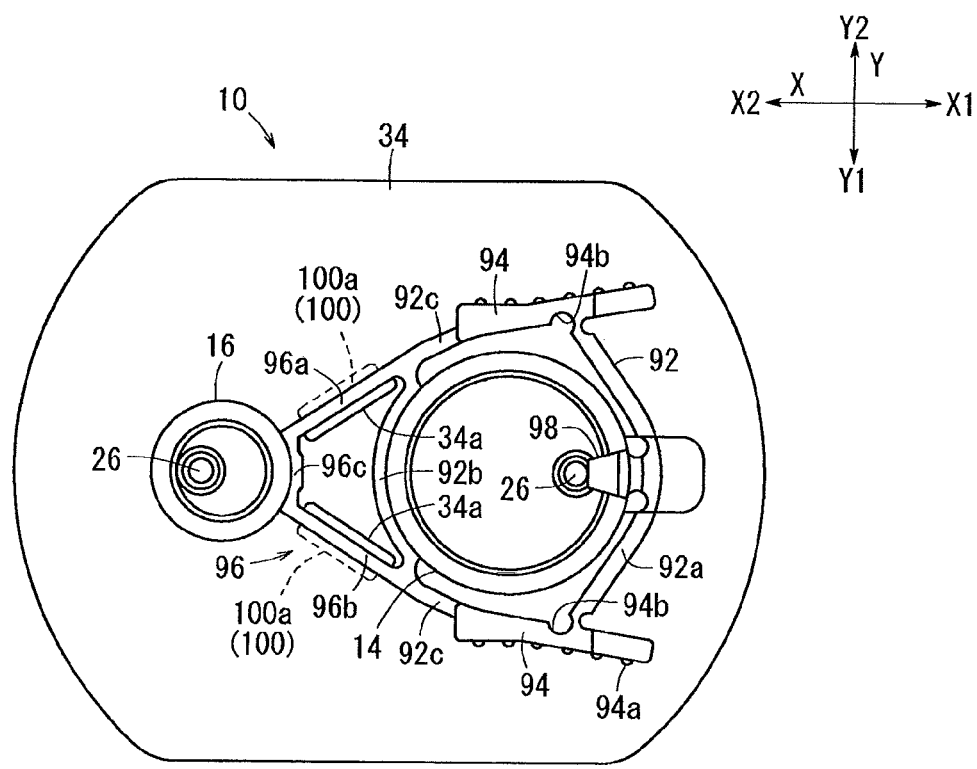
FIG. 3 is an explanatory side view illustrating a state in which a plunger is removed from an outer cylinder of the application instrument in FIG. 1.

FIG. 3 is an explanatory drawing of the application instrument 12 in FIG. 1 illustrating a state in which the plunger 22 is removed from an outer cylinder, and FIGS. 4A-4C illustrate the stopper member 24. For reference, FIG. 3 and subsequent FIG. 5B, FIG. 5D, FIG. 7B, FIG. 7C, FIG. 8B and FIG. 8C illustrate the X1 side of the syringe aligned on the right side of the drawings for easy understanding of the drawings.

The stopper member 24 according to the first embodiment includes a mounting portion 92 mounted on the first outer cylinder 14 so that the mounting portion 92 surrounds the first outer cylinder 14 while the inner surface of the mounting portion faces the outer surface of the first outer cylinder, a pair of operating sections or portions 94 extending from side surface of the mounting portion 92, and a supporting portion 96 extending outward from the mounting portion 92 as illustrated in FIG. 3 and FIGS. 4A to 4C. Although the material of the stopper member 24 is not specifically limited, the efficiency of manufacture may be improved by using the same material as the first and second outer cylinders 14, 16.

The mounting portion 92 possesses a substantially circular shape in front view, and the inner diameter of the mounting portion 92 is slightly larger than the outer diameter of the first outer cylinder 14 (see FIG. 3). In other words, the mounting portion 92 has a configuration in which the inner peripheral surface comes partly into abutment with the first outer cylinder 14, and is configured to allow the first outer cylinder 14 to be fitted therein.

The mounting portion 92 includes an inwardly extending hook (locking portion) 98 on the inner peripheral surface of the side portion 92a in the X1 direction. The hook 98 is formed integrally with the mounting portion 92 on the proximal end side and projects obliquely from a base portion of the mounting portion 92 toward the distal end side of the side portion 92a. In other words, the distal end portion of the hook 98 is spaced apart from the inner peripheral surface of the mounting portion 92 by a certain distance, and is configured to be swingable about the base portion of the mounting portion 92 as a supporting point.

The pair of operating sections 94 are provided at two positions (+90°, −90°) shifted by approximately 90° with respect to the center at the hook 98 formed on the mounting portion 92. The operating sections 94 are provided so as to continue from the side portions 92c of the mounting portion 92, project slightly radially outward of the mounting portion 92, and extend partly in the direction of formation of the hook 98 (X1 direction). The operating section 94 is formed with a plurality of projecting ridges 94a on the side surface of the operating sections 94 parallel to the axial direction of the operating sections 94, and is configured to allow easier gripping of the pair of the operating sections 94 by one hand.

The mounting portion 92 having the operating sections 94 provided thereon is formed with a groove portion 94b in the axial direction on the inner peripheral surface thereof. When the pair of the operating sections 94 is pinched in the Y direction, the groove portion 94b facilitates transmission of the clipping force to the side portion 92a of the mounting portion 92 formed with the hook 98, and allows the side portion 92a to be pinched rather easily in the X1 direction.

The supporting portion 96 is a portion projecting in the X2 direction with respect to the outer peripheral surface of the side portion 92b of the mounting portion 92 facing the hook 98. Specifically, a pair of supporting sides 96a, 96b extend obliquely by a predetermined length so as to approach each other from the two side portions 92c of the mounting portion 92 which are formed continuously with the pair of operating sections 94, and an abutting side (abutting portion) 96c coupling the supporting sides 96a, 96b to each other is formed at an apex of the pair of the supporting sides 96a, 96b. The abutting side 96c possesses an arcuate shape so that the outer peripheral surface comes into surface contact with the outer peripheral surface of the second outer cylinder 16 as illustrated in FIG. 3. The abutting side (abutting portion) 96c coupling the supporting sides 96a, 96b to each other is formed at an apex of the pair of the supporting sides 96a, 96b. The abutting side 96c thus connects together the ends of the supporting sides 96a, 96b projecting away from the mounting portion 92, and the curved outer surface of the abutting side 96c contacts the outer surface of the second outer cylinder 16.

Also, fixing parts (projecting portion) 100 projecting axially in the direction toward the distal end (Z1 direction) are formed at side edge portions on the distal end sides of the pair of the supporting sides 96a, 96b. The fixing parts 100 are longer than the plate thickness of the flange 34, and outwardly projecting claw portions 100a are provided at the distal ends of the fixing parts 100.

As illustrated in FIG. 3, in a state in which the stopper member 24 is mounted on the syringe 10, the inner peripheral surface of the side portion 92b of the mounting portion 92 come partly into abutment with the outer peripheral surface of the first outer cylinder 14, and the outer peripheral surface of the abutting side 96c abuts the outer peripheral surface of the second outer cylinder 16. The pair of fixing parts 100 is inserted into a pair of hole portions 34a (see FIG. 3) formed on the flange 34, and the claw portions 100a are exposed from opposite surfaces to achieve a locked state with the flange 34.

In this case, in the stopper member 24, the abutting side 96c abutting against the second outer cylinder 16, the supporting sides 96a, 96b to be fixed by the two fixing parts 100, and the side portion 92b of the mounting portion 92 in abutment with the first outer cylinder 14 compete against one another. Therefore, in the mounted state of the mounting portion 92, a state in which only the inner peripheral surface of the side portion 92b comes into abutment with the first outer cylinder 14, and other side portions 92a, 92c are spaced apart from the outer peripheral surface of the first outer cylinder 14 is assumed, and the stopper member 24 is fixedly supported reliably at the mounted position without coming apart from the first outer cylinder 14 even in this state. Since the movement in the direction of rotation of the stopper member 24 is prevented by the supporting portion 96, the positioning of the hook 98 in the peripheral direction may reliably be performed.

The pair of the operating sections 94 are capable of moving closer to each other in the direction of the first outer cylinder 14 (Y direction) about the side portion 92b as a supporting point by the side portion 92c of the mounting portion 92 moving apart from the first outer cylinder 14 as described above.

Furthermore, the hook 98 is arranged at a position where the distal end of the hook 98 extends to a position near the proximal opening portion of the first outer cylinder 14 while also projecting inward of the inner diameter of the cylindrical portion 14a (the locking position A: see FIG. 5A) in a state in which the stopper member 24 is mounted on the first outer cylinder 14. Any one of the teeth 90a of the tooth portion 90 of the first rod 36 engages the hook 98 arranged at the locking position A.

The application instrument 12 having the syringe 10 according to the first embodiment is configured as described above. Set forth next is a description of the operation of the syringe 10.

FIGS. 5A-5C illustrate the stopper member 24, with FIG. 5A providing a cross-sectional view of the stopper member 24 and a peripheral portion of the stopper member in an enlarged scale, FIG. 5B providing a cross-sectional front view viewed from Z1 in the Z2 direction, FIG. 5C providing a cross-sectional view of a state in which the hook 98 of the stopper member 24 in FIG. 1 moves in a spaced apart manner, and FIG. 5D provides a cross-sectional front view corresponding to FIG. 5C.

As illustrated in FIGS. 5A and 5B, the syringe 10 is configured in such a manner that the hook 98 of the stopper member 24 is at the locking position A, and engages the teeth 90a in a normal state. The normal state here means a state in which the pair of operating sections 94 are not pinched by the fingers or the like of the operator, that is a state in which an unlocking operation is not performed and in which no force is applied.

In this case, the plunger 22 is allowed to move in the direction toward the distal end with respect to the first and second outer cylinders 14, 16, and the movement in the direction toward the proximal end is limited. In other words, in a state in which the hook 98 is arranged at the locking position A, when the tooth portion 90 (the plunger 22) moves in the direction toward the distal end, the hook 98 extending obliquely in the direction toward the distal end swings by being guided by the side of the teeth 90a on the distal end side. Therefore, the stopper member 24 is capable of slowing the movement in the direction toward the distal end as is without locking the teeth 90a with the hook 98. In contrast, when an attempt is made to move the tooth portion 90 (the plunger 22) in the direction toward the proximal end, the hook 98 extending obliquely with respect to the side of the teeth 90a on the rear end side engages the rear end side of the teeth 90a, and the hook 98 acts to resist proximal direction movement of the teeth 90a (the plunger 22). Therefore, the stopper member 24 is capable of preventing the movement of the tooth portion 90 (the plunger 22) in the direction toward the proximal end by the teeth 90a being locked by the hook 98.

In this manner, the syringe 10 is capable of preventing non-filled substance reliably from being sucked into the first and second outer cylinders 14, 16 and the plunger 22 from coming apart from the first and second outer cylinders 14, 16 by preventing the movement of the plunger 22 in the direction toward the proximal end by the movement preventing mechanism (the tooth portion 90 and the stopper member 24). As a result, the first and second liquids L1, L2 filled in the syringe 10 may be desirably retained.

When filling the first and second outer cylinders 14, 16 with the first and second liquids L1, L2, the movement of the plunger 22 in the direction toward the proximal end is allowed by performing the unlocking operation on the movement preventing mechanism. In the case of the stopper member 24 according to the first embodiment, as illustrated in FIG. 5C and FIG. 5D, the locking of the tooth portion 90 by the hook 98 may be released relatively easily by pinching the pair of operating sections 94 provided on the stopper member 24. Since the pinching of the pair of the operating sections 94 may be performed by a single one of the operator's hands (one hand), the first and second outer cylinders 14, 16 can be filled with liquid rather easily by using the other hand to move (draw) the plunger 22 in the direction toward the proximal end.

Specifically, the operation in association with the unlocking operation will be described. When the pair of operating sections 94 of the stopper member 24 is pinched by the operator, the pressing force (pinching force) is applied to the side portions 92c of the mounting portion 92 which continue from the operating sections 94, and the side portions 92c of the mounting portion 92 are caused to be pinched inward (radially inward). In this case, the side of the mounting portion at the side portion 92b is fixed by the supporting portion 96. That is, radially outward movement of the side of the mounting portion 92 at the side portion 92b is suppressed, and so the pinching of the side portions 92c is transmitted to the side portion 92a side on which the hook 98 is formed, whereby the side portion 92a can be bent significantly radially outward. Accordingly, the hook 98 formed at a center of the side portion 92a is reliably moved away (retracted) from the locking position A so that engagement between hook 98 and the teeth 90a is released. The syringe is thus shifted from the locked position shown in FIGS. 5A and 5B to the unlocked position shown in FIGS. 5C and 5D.

In association with the retraction of the hook 98 from the locking position A, the tooth portion 90 of the plunger 22 is released from being locked by the hook 98, so that the movement in the direction toward the proximal end is allowed. Therefore, the first and second outer cylinders 14, 16 may be filled with the first and second liquids L1, L2 by moving the plunger 22 in the direction toward the proximal end.

Then, after having completed the filling of the liquid, the stopper member 24 having flexibility is restored to its original shape or position by the resilient force of the stopper member 24 only by releasing the pair of the operating sections 94 from being pinched. In association with this operation of releasing the operating sections 94, the hook 98 retracted from the locking position A by the bending of the mounting portion 92 is automatically restored to the locking position A.

In this manner, in the syringe 10 according to the first embodiment, prevention of the movement of the plunger 22 in the direction toward the proximal end and allowing of the movement of the plunger 22 in the direction toward the proximal end can be switched by an operation as simple as pinching the pair of the operating sections 94 of the stopper member 24, so that the filling and discharging of the liquid by the syringe 10 are relatively easily performed.

FIGS. 6A-6C and 7A-7C illustrate a stopper member 150 of a syringe 10A according to a second embodiment. For reference, in the description of the second embodiment (and third embodiment) below, features which are the same are identified by common reference numerals, and a detailed description of such features is not repeated.

The syringe 10A according to the second embodiment is a modification of the syringe 10 of the first embodiment in the structure of the movement preventing mechanism (a plunger 152 and the stopper member 150). In other words, the tooth portion 154 provided on the plunger 152 is formed on the flat plate portion 40c extending in the X2 direction of the first rod 36 (see FIG. 7A).

The stopper member 150 is formed with a hook 158 on an inner peripheral surface of a side portion 156b of the mounting portion 156 in the X2 direction corresponding to the position where the tooth portion 154 is formed. Also, a pair of operating sections 160 are provided respectively at two positions shifted by approximately 90° about a center at the hook 158 and they are formed so that each of them partly extends in the direction of formation or direction of extension of the hook 158 (in the X2 direction) (see FIG. 6B).

Figure 6C:
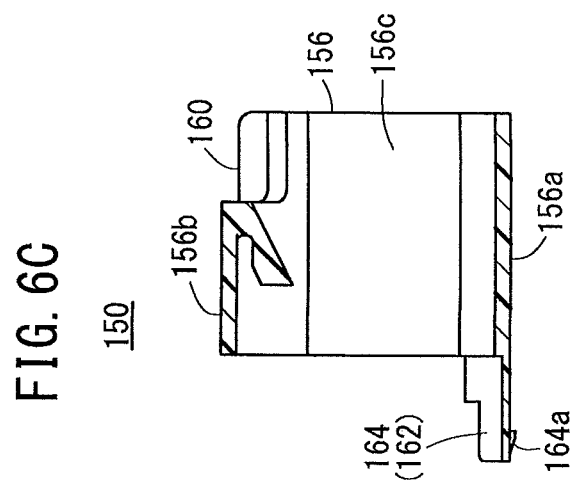
FIG. 6C is a cross-sectional view taken along the section line VIC-VIC in FIG. 6B.
Figure 6B:
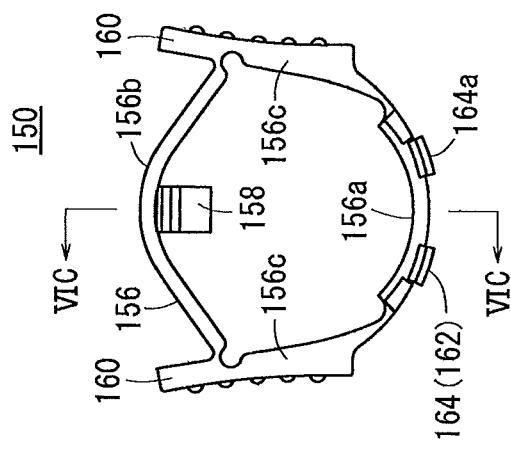
FIG. 6B is a front view illustrating a stopper member of the syringe according to the second embodiment.
Figure 6A:
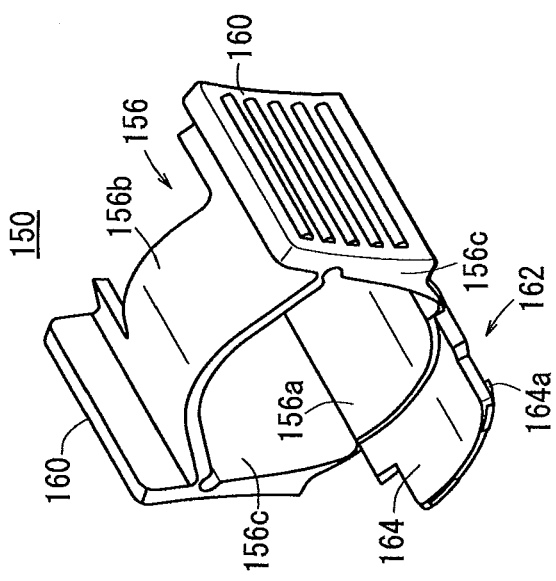
FIG. 6A is a perspective view illustrating a stopper member of a syringe according to a second embodiment.

The supporting portion 162 includes a fixing part 164 projecting in the direction toward the distal end from a distal end edge of a side portion 156a of the mounting portion 156 in the X1 direction as illustrated in FIG. 6A and FIG. 6C. The fixing parts 164 are longer than the plate thickness of the flange 34, and the distal ends of the fixing parts are provided with claw portions 164a extending outward.

Figure 7A:
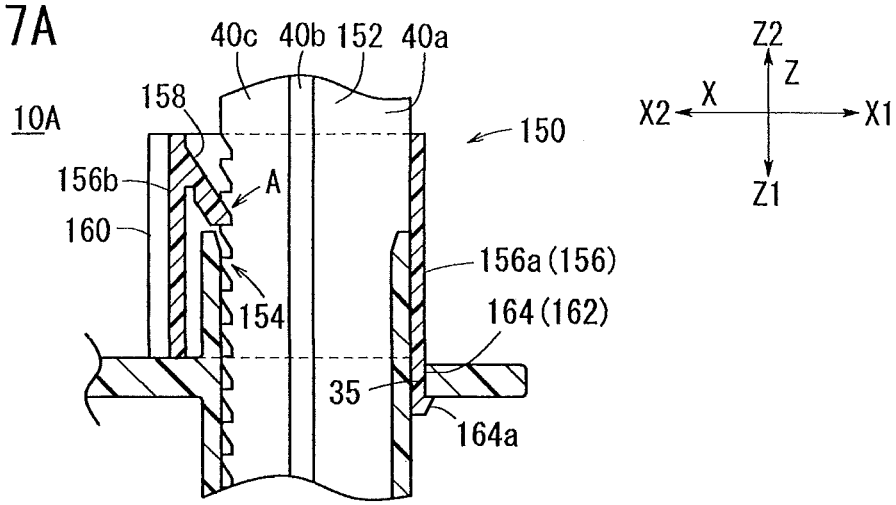
FIG. 7A is a partially enlarged cross-sectional view illustrating the stopper member in FIG. 6A and a peripheral portion thereof in an enlarged scale.
Figure 7B:
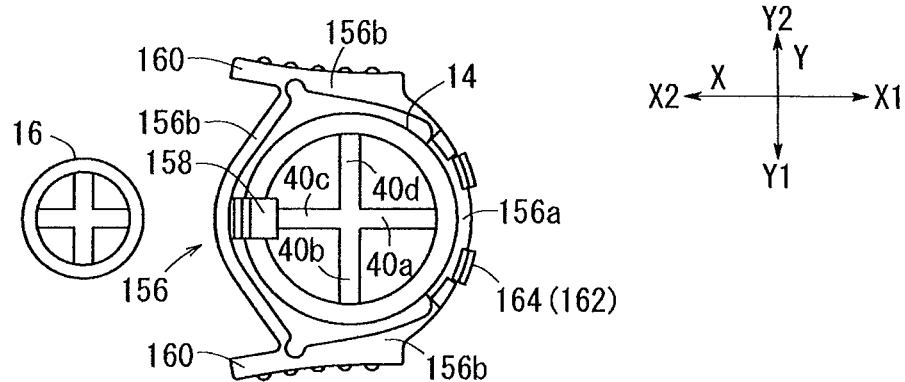
FIG. 7B is a cross-sectional front view corresponding to FIG. 7A.
Figure 7C:
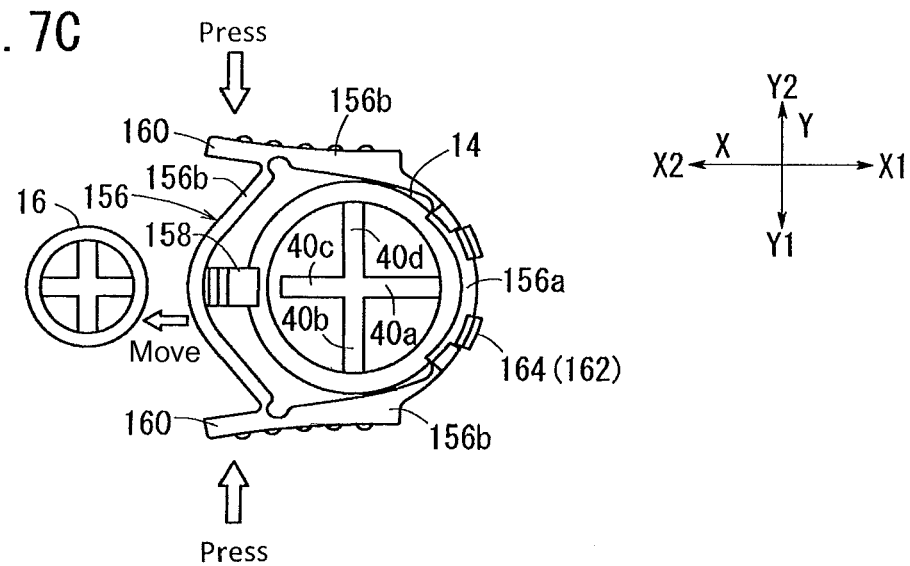
FIG. 7C is a cross-sectional front view illustrating a state in which a hook of the stopper member in FIG. 7B moves apart.

As illustrated in FIG. 7A and FIG. 7B, in a state in which the stopper member 150 is mounted on the first outer cylinder 14, the fixing part 164 is inserted into the hole portion 35 formed in the flange 34 and the claw portion 164a projects from the opposite surface, whereby the locked state with respect to the flange 34 is achieved. With the stopper member 150 according to the second embodiment, the fixing part 164 supports the side portion 156a of the mounting portion 156 in the X1 direction and hence the side portions 156b, 156c are configured so as to be spaced apart from the outer peripheral surface of the first outer cylinder 14.

The syringe 10A according to the second embodiment is formed as described above. Set forth next is a description of operational aspects of the syringe 10A. The syringe 10A is at the locking position A at which the hook 158 extends into the first outer cylinder 14 in the normal state, so that the tooth portion 90 are locked and the movement of the plunger 22 in the direction toward the proximal end is restricted. To effect the unlocking operation, the user operates the syringe by pinching the pair of operating sections 160 so that pressing forces applied to the pair of operating sections 160 are transmitted to the side portion 156b on which the hook 158 is formed via the side portion 156c of the mounting portion 156. This bends the side portion 156b radially outward, so that the hook 158 is retracted from the locking position A.

At this time, since the side portion 156a on the opposite side opposing the hook 158 is supported by the fixing part 164, the mounting portion 156 bends significantly only at the side portion 156b at which the hook 158 is located. Therefore, with the syringe 10A according to this second embodiment, effects similar to those discussed above with the first embodiment are realized.

Figure 8A:
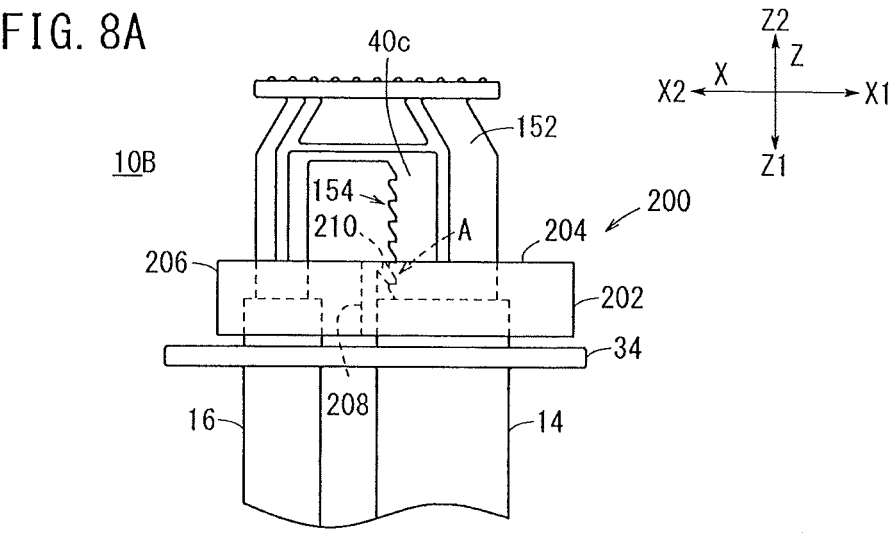
FIG. 8A is a partial plan view illustrating a syringe according to a third embodiment.
Figure 8B:
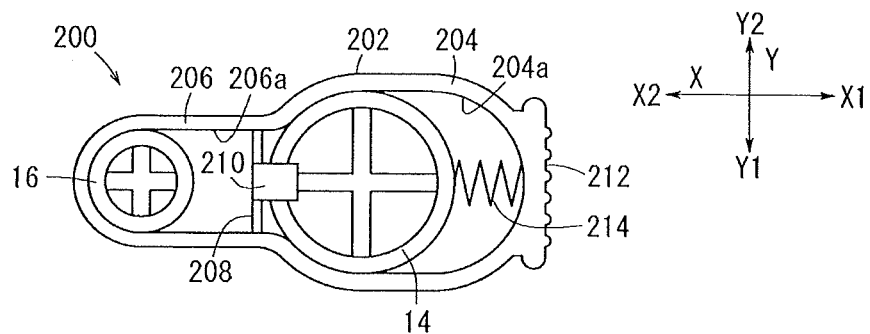
FIG. 8B is a cross-sectional front view corresponding to FIG. 8A.
Figure 8C:
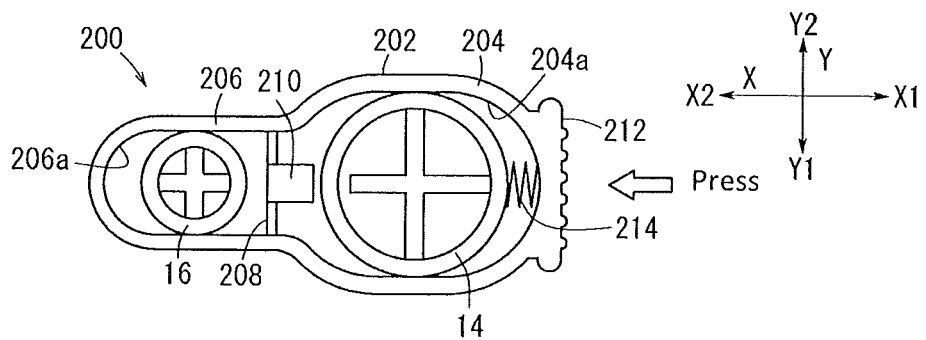
FIG. 8C is a cross-sectional front view illustrating a state in which a hook of the stopper member in FIG. 8B moves apart.

FIGS. 8A and 8B illustrating a syringe 10B according to a third embodiment. The syringe 10B according to the third embodiment differs from the syringes 10, 10A according to the first and second embodiments in that the stopper member 200 is configured to be integrally slidable. Since the plunger 152 of the movement preventing mechanism is configured in the same shape as the plunger 152 of the second embodiment, a detailed description is not repeated.

The stopper member 200 according to the third embodiment is formed with a mounting portion 202 configured so that the mounting portion surrounds the first and second outer cylinders 14, 16 integrally. Specifically, the mounting portion 202 includes a first mounting portion 204 which constitutes a first elongated hole 204a configured to engage an outer periphery of the first outer cylinder 14, and a second mounting portion 206 which constitutes a second elongated hole 206a engaging the outer diameter of the second outer cylinder 16 as illustrated in FIG. 8B. In other words, the first elongated hole 204a is guided by the first outer cylinder 14 and the second elongated hole 206a is guided by the second outer cylinder 16, so that the sliding movement of the stopper member 200 is restricted only in the X-direction according to the arrangement of the first and second outer cylinders 14, 16 in the X direction. A bridge portion 208 is continuously provided at a boundary portion between the first elongated hole 204a and the second elongated hole 206a of the mounting portion 202, and the hook 210 is formed on a surface facing the first outer cylinder 14 of the bridge portion 208.

The hook 210 locks the tooth portion 154 formed on the plunger 152 in the X2 direction in a state in which the stopper member 200 is positioned in the X1 direction, and prevents the movement of the plunger 152 in the direction toward the proximal end.

An operating section 212 configured to operate the sliding movement of the stopper member 200 is formed on the outer peripheral surface of the mounting portion 202 (the first mounting portion 204) in the X1 direction. Furthermore, a spring member (resilient member) 214 is interposed between the outer peripheral surface of the first outer cylinder 14 in the X1 direction and the inner peripheral surface of the first mounting portion 204 in the X1 direction. The spring member 214 is urged on the inner peripheral surface of the first mounting portion 204 in the X1 direction, and hence the entire portion of the stopper member 200 is urged in the X1 direction. Therefore, in the normal state, the stopper member 200 is positioned in the X1 direction and hence the hook 210 engages and locks the tooth portion 154 at the locking position in the normal state.

When unlocking the locking of the tooth portion 154 by the hook 210, the operating section 212 is pressed in the X2 direction as the unlocking operation, and the entire stopper member 200 is slid in the X2 direction. Accordingly, the hook 210 is retracted from the locked position of the tooth portion 154, and the movement of the plunger 152 in the direction toward the proximal end is allowed.

After the unlocking operation, the mounting portion 202 is urged by the spring member 214, whereby the stopper member 200 is restored to the original position. Accordingly, the hook 210 is automatically restored to the locking position. With this configuration of the syringe 10B, even with the spring member 214 provided between the mounting portion 202 and the first outer cylinder 14, the movement of the hook 210 (retraction to the locked position and restoration to the locked position) can be performed rather easily.

As described above, according to the syringes 10, 10A, 10B provided with the stopper members 24, 150, 200 of the first to the third embodiments, in a state in which the first and second outer cylinders 14, 16 are filled with the first and second liquids L1, L2, the hooks 98, 158, 210 of the stopper members 24, 150, 200 lock the tooth portions 90, 154 of the plungers 22, 152, whereby the movement of the plungers 22, 152 in the direction toward the proximal end is reliably prevented. Accordingly, the non-filled substance is prevented from entering the first and second outer cylinders 14, 16.

Also, by performing the simple unlocking operation with respect to the stopper members 24, 150, 200, movements of the plungers 22, 152 in the proximal direction is allowed, so that the filling or the like of the first and second outer cylinders 14, 16 with the first and second liquids L1, L2 is rather easily performed. In addition, by the restoration of the hooks 98, 158, 210 automatically to the locking position A after the unlocking operation, the hooks 98, 158, 210 can be locked to the tooth portions 90, 154 relatively easily without performing additional operation, so that the workability at the time of treating the syringes 10, 10A, 10B may be improved significantly.

Also, since the stopper members 24, 150, 200 are molded separately and configured to be demountably mountable, the stopper members 24, 150, 200 can be removed easily in a state in which the stopper members 24, 150, 200 are not required. In addition, since the shape of the syringe of the related art is not changed significantly at the time of molding, the manufacturing cost may be reduced.

The present invention is not limited to the embodiments described above, and various configurations and processes may be implemented without departing the scope of the present invention.

For example, even though the stopper member is not provided with the supporting portion, by selecting a material having relatively large flexibility to form the mounting portion and the hook, the hook may be moved (retracted) from the engaged portion by pressing predetermined side portions of the mounting portion. In other words, the stopper member is not limited to the structures of the first to the third embodiments as long as the hook can be retracted from the locking position in association with the unlocking operation and restored after the unlocking operation.

In the first to the third embodiment, the syringe 10, 10A, 10B having the two outer cylinders (the first and second outer cylinders 14, 16) is described. However, the invention may be applied to a syringe composed on one outer cylinder as a matter of course.

The detailed description above describes a syringe disclosed by way of several examples. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe comprising:
an outer cylinder possessing a distal end and a flowing port at the distal end of the outer cylinder through which liquid flows, the outer cylinder possessing an open proximal end and an inner surface surrounding an interior of the outer cylinder, the interior of the outer cylinder communicating with the flowing port, the outer cylinder possessing an outer surface;
a gasket positioned in the interior of the outer cylinder in liquid-tight contact with the inner surface of the outer cylinder and movable in a distal direction along the interior of the outer cylinder to discharge the liquid, which was previously introduced into the interior of the outer cylinder, through the flowing port;
a rod connected to the gasket so that the rod and the gasket move together as a unit, the rod extending through the open proximal end of the outer cylinder, the rod including a plurality of teeth arranged in spaced apart relation along the rod;
a mounting portion surrounding a proximal end portion of the outer cylinder and possessing an inner surface facing the outer surface of the outer cylinder, a hook fixed to the mounting portion and extending inwardly;

the hook engaging one of the teeth on the rod in a locking position of the hook to prevent the rod from moving in the proximal direction relative to the outer cylinder;

an operating portion fixed to the mounting portion and operable by a user pressing the operating portion to move the hook from the locking position in which the hook engages one of the teeth to an unlocking position in which the hook is moved out of engagement with the teeth to permit the rod to move in the proximal direction, the hook automatically returning to the locking position when the operating portion is no longer pressed by the user; and wherein the mounting portion is annular-shaped, and the operating portion is comprised of a pair of operating sections fixed relative to the annular-shaped mounting portion at diametrically opposite positions.

2. The syringe according to claim 1, wherein the hook is fixed to an inner peripheral surface of the mounting portion.

3. The syringe according to claim 1, further comprising a supporting portion fixed to the mounting portion at a side of the mounting portion opposite the hook, the supporting portion extending outwardly away from the mounting portion and configured to suppress radially outward movement of the side of the mounting portion opposite the hook when the operating portion is pressed.

4. The syringe according to claim 3, wherein the outer cylinder is a first outer cylinder possessing a central axis and an outer peripheral surface, and further comprising a second outer cylinder possessing a central axis and an outer peripheral surface, the first and second outer cylinders being arranged side by side in which the central axis of the first outer cylinder is parallel to the central axis of the second outer cylinder.

5. The syringe according to claim 4, wherein the supporting portion includes an abutting portion in contact with the outer peripheral surface of the second outer cylinder.

6. The syringe according to claim 1, wherein the outer cylinder is a first outer cylinder possessing a central axis and an outer peripheral surface, and further comprising a second outer cylinder possessing a central axis and an outer peripheral surface, the first and second outer cylinders being arranged side by side in which the central axis of the first outer cylinder is parallel to the central axis of the second outer cylinder.

7. The syringe according to claim 1, further comprising a supporting portion fixed to the mounting portion, and a flange fixed to the outer cylinder and extending radially outward from the outer cylinder at a position toward the proximal end of the outer cylinder, the flange including a through hole, and the supporting portion including a projecting portion positioned in the through hole in the flange.

8. A syringe comprising:

an outer cylinder having a flowing port at a distal end of the outer cylinder through which liquid flows, the outer cylinder possessing an interior;

a plunger insertable into the outer cylinder from a proximal end of the outer cylinder to push out the liquid in the interior of the outer cylinder through the flowing port by movement of the plunger in a movement direction toward the distal end of the outer cylinder;

a tooth portion provided on the plunger and arranged along the movement direction of the plunger;

a locking portion configured to lock the tooth portion at a locking position to prevent the plunger from moving in a proximal direction away from the distal end of the outer cylinder;

the locking portion is retracted from the locking position in response to an unlocking operation, and is automatically restored to the locking position after the unlocking operation, and the locking portion includes a hook formed integrally with a flexible stopper member mounted on the outer cylinder so that the hook is positioned at the locking position;

wherein the stopper member includes a mounting portion surrounding the outer peripheral surface of the outer cylinder, and a plurality of operating sections extending so as to be spaced apart radially outward from an outer peripheral surface of the mounting portion; and wherein the hook is located on an inner peripheral surface of the mounting portion, and moves radially outward out of engagement with the tooth portion to retract from the locking position when the operation sections are pinched towards one another during the unlocking operation.

9. The syringe according to claim 8, wherein the stopper member includes a supporting portion fixed to the mounting portion at a side of the mounting portion opposite the hook, the supporting portion extending outwardly away from the mounting portion and configured to suppress radially outward movement of the side of the mounting portion opposite the hook when the operation sections are pinched towards one another during the unlocking operation.

10. The syringe according to claim 9, wherein the outer cylinder is a first outer cylinder possessing a central axis and an outer peripheral surface, and further comprising a second outer cylinder possessing a central axis and an outer peripheral surface, the first and second outer cylinders being arranged side by side so that the central axis of the first outer cylinder is parallel to the central axis of the second outer cylinder, and the supporting portion including an abutting portion in contact with the outer peripheral surface of the second outer cylinder.

11. The syringe according to claim 9, further comprising a flange fixed to the outer cylinder and extending radially outward from the outer cylinder at a position toward the proximal end of the outer cylinder, the flange including a through hole, and the supporting portion including a projecting portion positioned in the through hole in the flange.

12. A syringe comprising:

an outer cylinder possessing a distal end and a flowing port at the distal end of the outer cylinder through which liquid flows, the outer cylinder possessing an open proximal end and an inner surface surrounding an interior of the outer cylinder, the interior of the outer cylinder communicating with the flowing port, the outer cylinder possessing an outer surface;

a gasket positioned in the interior of the outer cylinder in liquid-tight contact with the inner surface of the outer cylinder and movable in a distal direction along the interior of the outer cylinder to discharge the liquid, which was previously introduced into the interior of the outer cylinder, through the flowing port;

a rod connected to the gasket so that the rod and the gasket move together as a unit, the rod extending through the open proximal end of the outer cylinder, the rod including a plurality of teeth arranged in spaced apart relation along the rod;

a mounting portion surrounding a proximal end portion of the outer cylinder and possessing an inner surface facing the outer surface of the outer cylinder, a hook fixed to the mounting portion and extending inwardly;

the hook engaging one of the teeth on the rod in a locking position of the hook to prevent the rod from moving in the proximal direction relative to the outer cylinder;

an operating portion fixed to the mounting portion and operable by a user pressing the operating portion to move the hook from the locking position in which the hook engages one of the teeth to an unlocking position in which the hook is moved out of engagement with the teeth to permit the rod to move in the proximal direction, the hook automatically returning to the locking position when the operating portion is no longer pressed by the user; and a supporting portion fixed to the mounting portion at a side of the mounting portion opposite the hook, the supporting portion extending outwardly away from the mounting portion and configured to suppress radially outward movement of the side of the mounting portion opposite the hook when the operating portion is pressed.

* * * * *